(12) United States Patent
Jentsch et al.

(10) Patent No.: US 6,656,117 B2
(45) Date of Patent: Dec. 2, 2003

(54) APPARATUS AND SYSTEM FOR MONITORING OBJECTS CONTAINED INSIDE A LIVING BODY

(75) Inventors: Klaus Jentsch, Schwaig (DE); Gunter C. W. Lob, Munich (DE)

(73) Assignee: Lmb Technologie GmbH, Schwaig (DE)

( * ) Notice: Subject to any disclaimer, the term of this patent is extended or adjusted under 35 U.S.C. 154(b) by 0 days.

(21) Appl. No.: 10/020,191

(22) Filed: Dec. 18, 2001

(65) Prior Publication Data

US 2002/0091310 A1 Jul. 11, 2002

(30) Foreign Application Priority Data

Jan. 5, 2001 (DE) .......................................... 101 00 324

(51) Int. Cl.7 .................................................. A61B 5/00
(52) U.S. Cl. ....................................... 600/300; 128/903
(58) Field of Search ................................. 600/300–302; 128/897–899, 903, 904; 700/108–110; 702/182–186; 340/3.43, 3.44; 607/27–29

(56) References Cited

U.S. PATENT DOCUMENTS

| 5,970,986 A | 10/1999 | Bolz et al. |
| 6,285,285 B1 | 9/2001 | Mongrenier |
| 6,475,443 B1 | 11/2002 | van Deursen et al. |

FOREIGN PATENT DOCUMENTS

| DE | 0 706 825 A1 | 4/1996 |
| DE | 196 07 222 A1 | 8/1997 |
| DE | 196 21 179 A1 | 11/1997 |
| DE | 403 245 B | 12/1997 |
| DE | 196 38 585 A1 | 3/1998 |
| DE | 0 875 292 A1 | 11/1998 |
| FR | 2 796 182 A | 1/2001 |
| WO | WO 99/53467 | 10/1999 |
| WO | WO 00 42969 A | 7/2000 |

*Primary Examiner*—Eric F. Winakur
*Assistant Examiner*—David J. McCrosky
(74) *Attorney, Agent, or Firm*—Oliff & Berridge, PLC (57) ABSTRACT

There is disclosed an apparatus for monitoring objects contained inside a living body, wherein the apparatus includes a transmitter/receiver device which is introduceable into the living body and in which data relating to the object may be stored, wherein the data relating to the object may be written into the transmitter/receiver device and read from it contactless with the aid of an external write-read device located externally of the living body, and includes at least one sensor device for monitoring the at least one temporally variable state parameter of the object and for transmitting data corresponding to a currently prevailing state to the transmitter/receiver device in accordance with a detected value of the temporally variable state parameter, wherein the data corresponding to the currently prevailing state is written into the transmitter/receiver device in response to transmission from the sensor device. In addition, there is disclosed a system for monitoring objects contained inside a living body.

14 Claims, 8 Drawing Sheets

APPARATUS AND SYSTEM FOR MONITORING OBJECTS CONTAINED INSIDE A LIVING BODY

BACKGROUND OF THE INVENTION

1. Field of the Invention

The present invention relates to an apparatus and a system for monitoring objects contained inside a living body.

2. Description of the Prior Art

Various grave problems occur in various areas of medicine when objects foreign to the body, such as implants or transplants or the like, are introduced into the body. Rejection phenomena against a transplanted organ may, for instance, occur after a transplantation, or an artificial implant such as a prosthesis may shift its position or come loose in the course of time, and infections may occur in either one of these cases.

The like problems hitherto needed to be recognized at an early point of time with the aid of various examinations such as, e.g., ultrasound examinations, X-ray examinations, etc., or else they are prevented by administering medicaments as is, for instance, the case with organ transplantations.

Although such measures frequently do constitute a strong physical and/or psychological stress to the patients in question, the measures as such nevertheless are indispensable.

SUMMARY OF THE INVENTION

Accordingly, it is the object of the present invention to create an apparatus and a system for monitoring objects contained inside a living body, whereby physical and/or mental stress to these patients is reduced.

According to an aspect of the present invention an apparatus for monitoring objects contained inside a living body includes a transmitter/receiver device which is introduceable into the living body and in which data relating to the object may be stored, wherein the data relating to the object may be written into the transmitter/receiver device and read from it contactless with the aid of an external write-read device located externally of the living body; and at least one sensor device for monitoring at least one temporally variable state parameter of the object and for transmitting data corresponding to a currently prevailing state to the transmitter/receiver device in accordance with a detected value of the temporally variable state parameter. The data corresponding to the currently prevailing state are written into the transmitter/receiver device in response to transmission from the sensor device.

In accordance with the invention it was recognized that for monitoring an object contained inside a living body it is advantageous to detect a temporally variable state parameter of the object and to write data corresponding to a currently prevailing state into the transmitter/receiver device.

Just the same, the data relating to the object may be primary characteristic data of the object which are available for use by various authorized persons in different locations, such as physicians, as a result of their being stored in the transmitter/receiver device.

Thanks to the above mentioned measures it is possible to also process, besides the data relating to the object, data corresponding to the currently prevailing state, whereby a simple examination possibility from outside of the living body is provided through the external write-read device, without a patient being subjected to high stress. Due to the possibility of continuously verifying the temporally variable state parameter, a verifying possibility is moreover improved considerably.

Moreover it is possible to recognize negative developments concerning the object from early on, so that it is furthermore possible to create a quality management of implants and transplants, whereby follow-up costs such as through additional surgery may be avoided.

In accordance with one development of the present invention, the outside of the apparatus is surrounded by a physiologically compatible material or comprised thereof.

In accordance with another development of the present invention, the object is a transplant or an implant or some other natural or artificial part or replacement part.

In accordance with another development of the present invention, the data corresponding to the currently prevailing state, which is stored in the transmitter/receiver device, is readable with the aid of the external write-read device.

In accordance with another development of the present invention, the transmitter/receiver device is a transponder or a bluetooth chip.

In accordance with another development of the present invention, the sensor device detects a value of a physical function, a value of a physiological function, or a combination of these as the temporally variable state parameter.

In accordance with another development of the present invention, the apparatus moreover includes a fixing means whereby it may be fixed inside the living body.

In accordance with another development of the present invention, the data corresponding to the currently prevailing state is directly written into the transmitter/receiver device in response to transmission from the sensor device.

In accordance with another development of the present invention, the data corresponding to the currently prevailing state is written into the transmitter/receiver device by means of the external device in response to transmission from the sensor device.

Moreover by means of the apparatus according to the invention and an external write-read device it is possible to create a system for monitoring objects contained inside a living body, with this system having features that are equivalent to those in relation with the above described apparatus.

BRIEF DESCRIPTION OF THE DRAWINGS

These and other aspects of the present invention will be apparent from and elucidated with reference to the embodiments described hereinafter and considered in connection with the accompanying drawings, in which.

DETAILED DESCRIPTION OF THE INVENTION

The following is a description of a first embodiment of the present invention.

Figure 1:
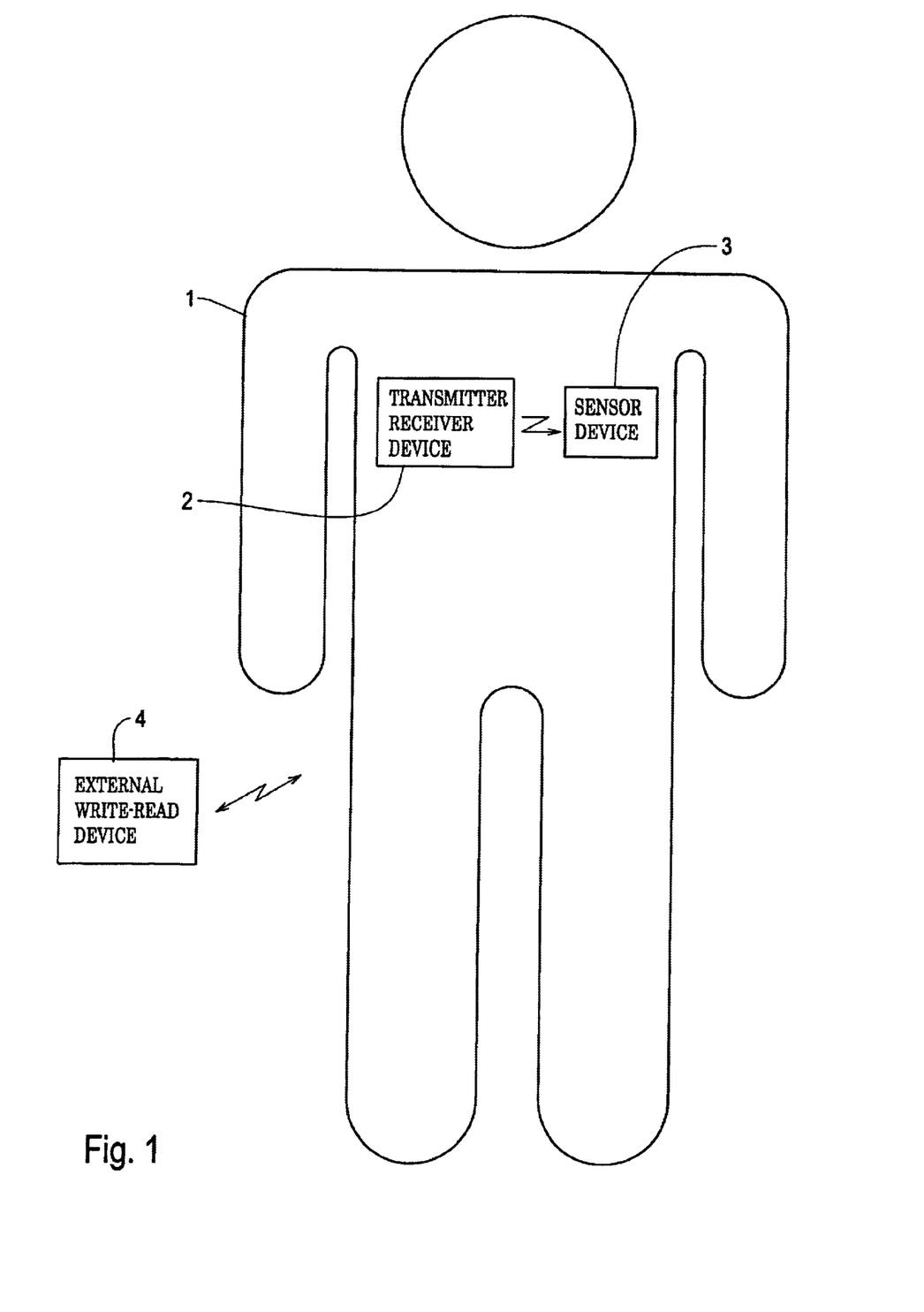
FIG. 1 shows a schematic representation of an apparatus in accordance with a first embodiment of the present invention.

In FIG. 1, reference numeral 1 designates a symbolic representation of a living body, reference numeral 2 designates a transmitter/receiver device, reference numeral 3 designates a sensor device, and reference numeral 4 designates an external write-read device.

In application, at least the transmitter/receiver device 2 is located within the living body 1, and the external write-read device 5 is located externally of the human body, as is indicated in FIG. 1 by the living body 1.

As the transmitter/receiver device 2 it is possible to use, for example, a transponder or a bluetooth chip. It is, however, also possible to use another device than the transmitter/receiver device 2 as long as there exists a possibility of writing data from outside of the living body 1 into the transmitter/receiver device 2 located within the living body 1, and to read it from the latter into the external write-read device 4 from inside the living body 1 to the outside of the living body 1.

Depending on the kind of transmitter/receiver device 2 employed, a suitable external write-read device 4 is used. If a transponder is employed as the transmitter/receiver device 2, then an external transponder write-read device is used as the external write-read device 4; if a bluetooth chip is employed as the transmitter/receiver device 2, then an external bluetooth write-read device is used as the external write-read device 4, etc.

As the sensor device 3 any sensor suitable for the application at hand may be used, which is capable of detecting a value of a temporally variable state parameter to be detected of a respective object to be monitored. In this embodiment of the present invention, the values of the temporally variable state parameter of an object to be monitored as detected by the sensor device 3 are directly transmitted to the transmitter/receiver device 2 and stored therein, as is shown by the arrow between the transmitter/receiver device 2 and the sensor device 3 in FIG. 1. Such state parameters to be detected may, e.g., be respective physiological or physical functions within the living body 1 which may moreover relate to states of artificial parts or replacement parts, as shall be described in more detail hereinbelow. The respective sensor devices 3 used may be both active sensor devices which require an energy supply source of their own, and passive sensor devices which do not require an energy supply source of their own and operate, for instance, like a transponder with an externally coupled, separate energy supply. The like sensor devices 3 for detecting values of the above described functions are well known in medical technology and shall not be described here any further; it is, however, noted that sensor devices may be used which can detect state parameters of liquid objects such as, e.g., blood, or of gaseous objects inside the living body, if this should be required for the application at hand.

The following is a description of the construction of the first embodiment of the present invention.

As is shown in FIG. 1, the transmitter/receiver device 2 is located within a living body 1 while being positioned in a location that is suited for monitoring a particular object. The transmitter/receiver device 2 is comprised of a material which is physiologically compatible, or is surrounded by such a material. The like materials must have the ability of permitting communication from within the living body 1 to outside of the living body 1 and include, for example, polymer resins, polyethylene, polyacetate, polytetrafluoroethylene, glass ceramics, etc. In the first embodiment of the present invention, the transmitter/receiver device 2 and the sensor device 3 are both introduced inside the living body 1 and may be accommodated either in a single housing or else in different housings, as long as the entire apparatus altogether is comprised of a physiologically compatible material or covered by it. Moreover the entire apparatus includes fixing means (not shown) whereby the entire apparatus may be fixed inside the human body 1. Such fixing means may, for example, be implemented by means of a physiologically compatible adhesive whereby the entire apparatus may be fixed to a bone or the like. Other types of fixing means are, however, also possible.

It should moreover be noted that—although only a transmitter/receiver device 2 and a sensor device 3 are shown in FIG. 1—there is the option as well of using several other transmitter/receiver devices 2 and/or sensor devices 3 which may either be integrated with each other or separate from each other. Finally there is provided the external write-read device 4 which is located externally of the living body 1 and may be connected with external processing means (not shown) such as, for example, a diagnostic computer, a computer or the like by wireless connection or by means of a suitable, e.g. optically or electrically conductive connection. The external processing means, in turn, may be connected with a computer network or the like by wireless connection or by means of a suitable, e.g. optically or electrically conductive connection.

The following is a description of the operation of the first embodiment of the present invention.

As was already mentioned, the present invention is designed for monitoring an object within the living body 1. Such an object may be a transplanted organ, an artificial organ, but also any other natural or artificial body replacement part, such as a prosthesis or the like. Depending on the object to be monitored, values of physiological functions and/or values of physical functions are monitored as a temporally variable state parameter by means of suitable sensor devices 3. 'Physiological functions' here should, e.g., be understood as chemical and/or biochemical reactions relating to respective objects, and 'physical functions' should be understood as mechanical reactions relating to respective objects.

Examples which may be given for such objects to be monitored are heart, kidney and other organs and any artificial body replacement parts such as, e.g., artificial organs and prostheses. In the case of the heart, for example, the heartbeat may be detected by the sensor device 3 and transmitted into the transmitter/receiver device 3 to be stored therein. In the case of the prosthesis or of another implant, for example, the sensor device 3 may detect a positional change of the prosthesis, such as a shrinkage of the prosthesis, as measurement points with the aid of transmitter/receiver devices 2, and transmit corresponding data from the sensor device 3 to the transmitter/receiver device 2 and store them therein. This application shall be described in more detail further below. It is, however, noted that in this application the sensor device 3 is arranged externally of the living body 1, which will also be explained further below.

When the apparatus according to the invention is to be used, known data relating to the organ or to a patient is written contactless into the transmitter/receiver device with the aid of the external write-read device 5, Such data known beforehand may also be written into the transmitter/receiver device 3 with the aid of the external write-read device 4 prior to introducing the apparatus into the living body. This data will then be available in subsequent monitoring processes and say be read from the transmitter/receiver device 2 by means of a respective external write-read device 4 and subjected to further processing, may be supplemented with additional data, modified, or deleted. Such data relating to the object constitutes primary characteristic data or other data of transplants or implants which may be retrieved contactless at any time in any place. This data includes, for example, data concerning surgery, such as date, time, place, clinic, physician in charge, next examination date etc., data concerning the implant or transplant, such as, e.g., manufacturer, serial number, date of manufacture etc., and/or data concerning a patient, such as, e.g., insertion height 1 of an implant, insertion height 2 of an implant, etc., and optionally further data such as, e.g., date, time, place, a specialist's clinic, attending physician, next examination date, findings, etc. This data is used for drawing up a maintenance and/or life history of the transplant or implant, which may readily be retrieved in any place at any time.

Besides such data relating to the object or to the patient, the sensor device 3 may at any time and at any intervals detect a value of a currently prevailing state parameter and directly write it into the transmitter/receiver device 3, either contactless or through the intermediary of a suitable connection, e.g. an electrically or optically conductive one. A respective detected value of a temporally variable state parameter of the object may then, as well, be used and processed at any point of time similarly to the above described data relating to the object.

The external write-read device 4 may be connected with a processing means (not shown), such as a diagnostic computer, a computer connected to a computer network or the like, either by wireless connection or by means of a suitable connection, e.g. an electrically or optically conductive one in accordance with the above description, so that via the external write-read device 4 there is the possibility both of writing data from the external processing means 4 into the transmitter/receiver device 2, and to also read it from there in order to carry out various kinds of processing.

Thanks to the above described apparatus there exists the possibility of simplifying a diagnosis concerning the object by making use of values of the temporally variable state parameter, and there also exists a possibility, if it is a matter of an artificial object, to generate the life history and/or maintenance file for the object to be monitored and write it into the transmitter/receiver device 2 and read it therefrom. Generally speaking, data relating to an object may be written on the transmitter/receiver device 2, processed with the aid of an external computer or computer network, modified and/or supplemented, and again written into the transmitter/receiver device 2.

The present invention is excellently suited for monitoring most variegated objects within a living body 1.

The following is a description of a second embodiment of the present invention.

Figure 2:
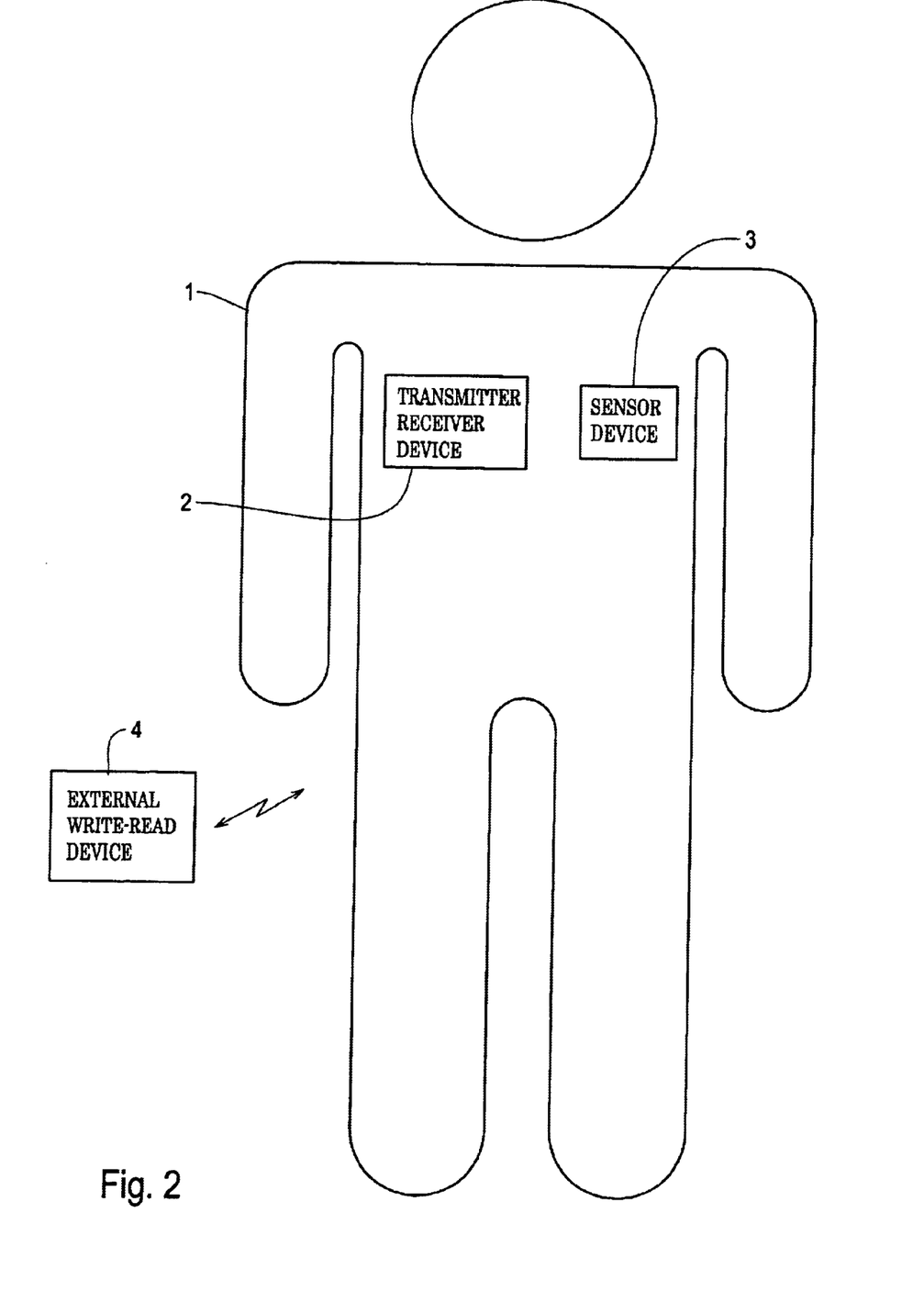
FIG. 2 shows a schematic representation of an apparatus in accordance with a second embodiment of the present invention.

The second embodiment of the present invention, as shown in FIG. 2, differs from the first embodiment of the present invention in that the sensor device 3 transmits respective values of the temporally variable state parameter from the sensor device 3 to the external write-read device 4 not directly, but indirectly contactless through the intermediary of the external write-read device 5, which values are then stored by the latter in the transmitter/receiver devices 2. As a result, respective data corresponding to values of the temporally variable state parameter of an object to be monitored may only be written into the transmitter/receiver device 2 when the external write-read device 4 is present.

The further operation of the second embodiment and the further possibilities of processing the data relating to the object and the data corresponding to the value of the temporally variable state of the object are identical with that of the first embodiment of the present invention, so that a detailed description is omitted in this place.

The following is a description of a third embodiment of the present invention.

Figure 3:
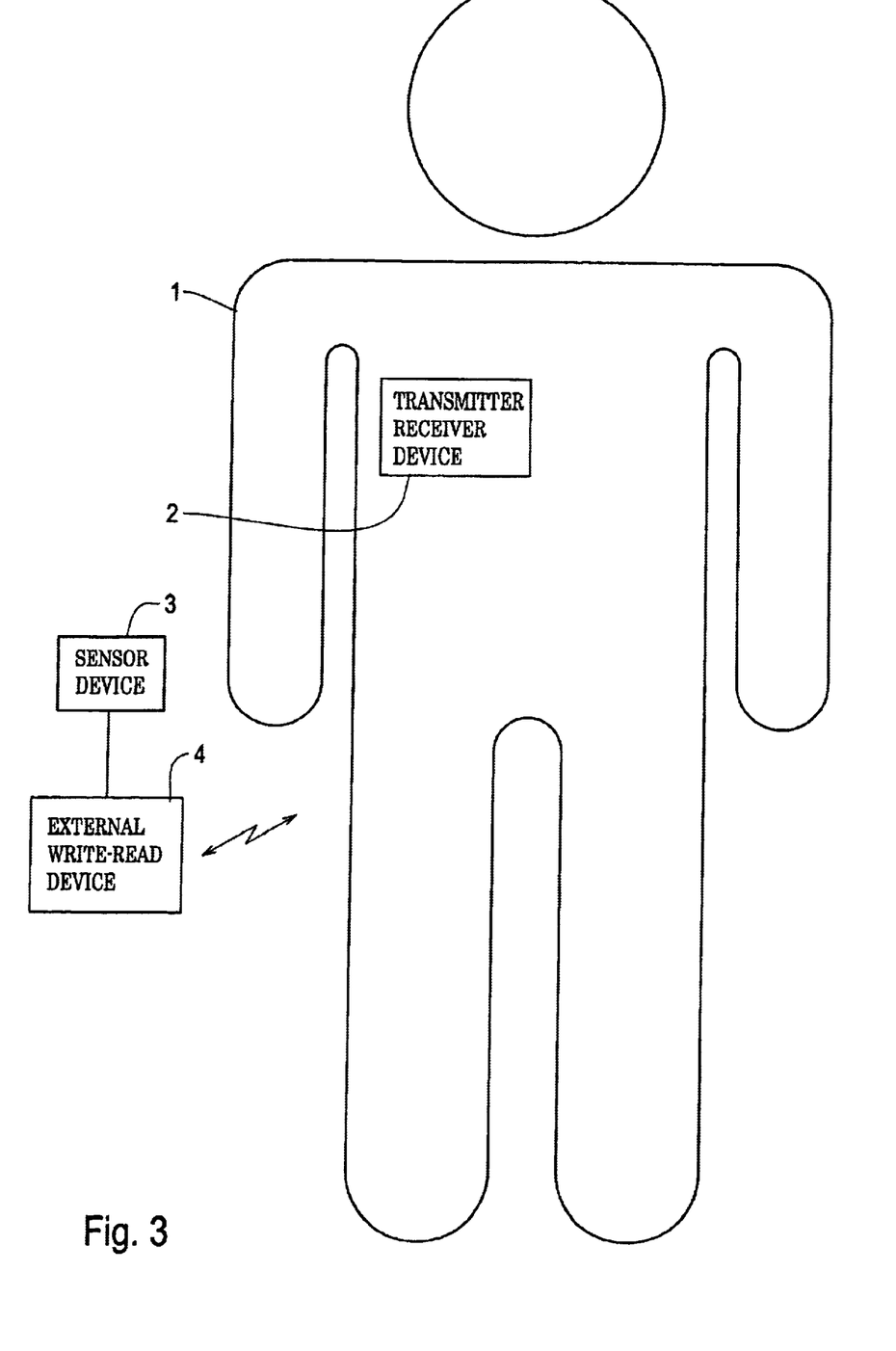
FIG. 3 shows a schematic representation of an apparatus in accordance with a third embodiment of the present invention.

The third embodiment of the present invention differs from the second embodiment of the present invention in that the sensor device 3 is arranged externally of the living body 1. The sensor device 3 detects the data relating to the temporally variable state, either directly as in the first embodiment of the present invention, or indirectly as in the second embodiment of the present invention via the external write-read device 4 to the transmitter/receiver device 2, in which it is stored.

The further operation of the third embodiment and the further possibilities of processing the data relating to the object and the data corresponding the value of the temporally variable state of the object are identical with the first and second embodiments of the present invention, so that a detailed description thereof is omitted here.

The following is a description of developments of the first through third embodiments of the present invention.

Each transmitter/receiver device 2 may have an unambiguous serial number. If, now, in a particular location such as a clinic, several patients with the apparatus according to the invention are present, it is possible to select by means of the external write-read device 4 while taking into consideration a respective serial number, which transmitter/receiver device 2 is to be addressed through the external write-read device 4 in order to write data into it or read from there. Thanks to such a serial number, data collision and/or inadvertent addressing of a wrong transmitter/receiver device 2 may be prevented.

With the aid of an unambiguous serial number it is moreover possible to simultaneously query a plurality of transmitter/receiver devices 2 which are to be queried, by allocating a particular serial number to a group of transmitter/receiver devices 2 to be queried, in order to store data in them or read from them.

Each external write-read device 4 may moreover have several channels, whereby it is possible to simultaneously query several transmitter/receiver devices 2 in order to write different data into them or read it from them.

The apparatus according to the invention may moreover be coupled with other devices in the body, performing, e.g., release of medicaments in the body. In this case the sensor device 3 detects, for example, a value of a temporally variable parameter relating to release of a medicament. Such an application would, for example, be an implanted insulin pump, with the sensor device 3 then possibly detecting, for example, a dose of the insulin or an insulin value of the person carrying the insulin pump.

The following is a description of an application of the present invention.

This application relates to a positional change of an implant, preferably a prosthesis or artificial joint. It is, however, readily apparent that this application may also be employed with other implants and transplants.

Figure 4A:
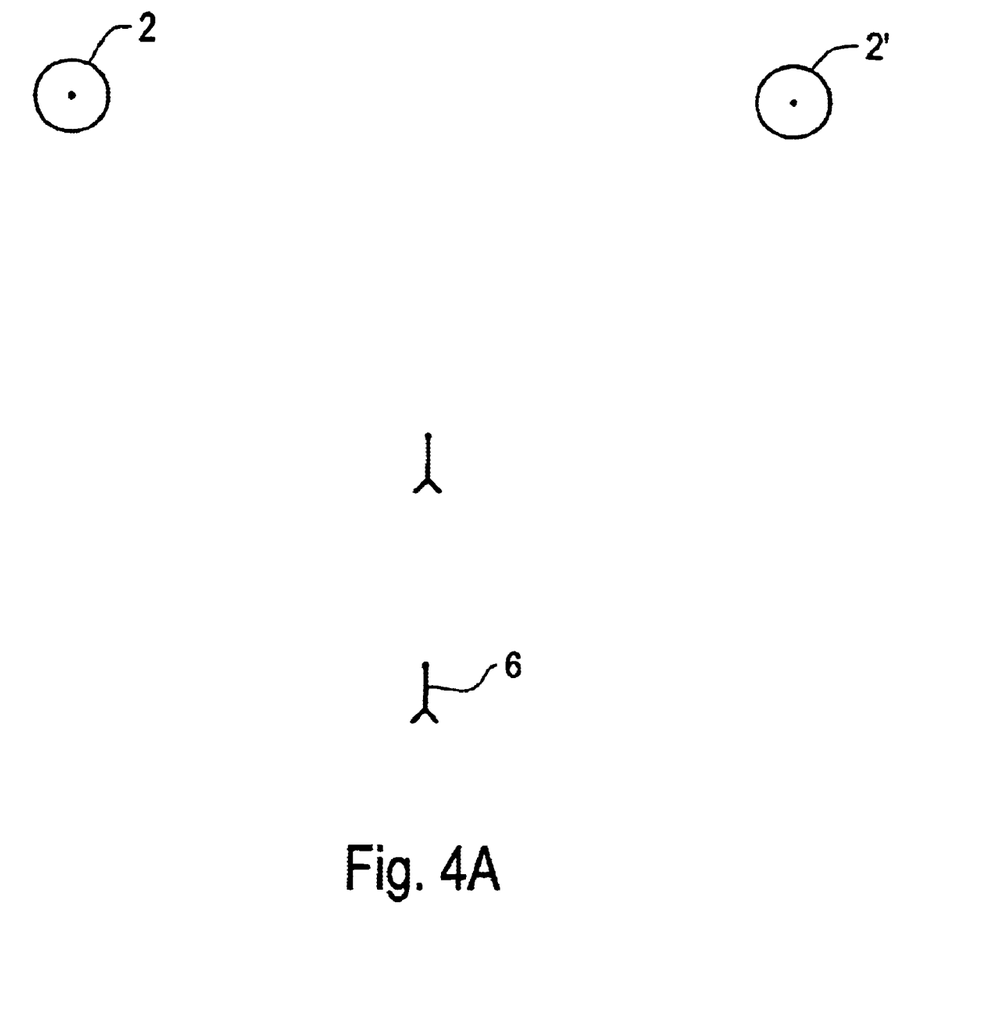
FIGS. 4A to 4E show an application of the present invention to an implant.

As is shown in FIG. 4A, a first transmitter/receiver device 2 is provided. This first transmitter/receiver device 2 is fixedly attached, e.g. to a bone stump, as a fixed point of reference. Moreover a second transmitter/receiver device 2' is provided, which is attached to a prosthesis or to an artificial joint. Moreover the sensor device 3 includes a multiple-window antenna 6 preferably arranged externally of the living body 1, whereby a distance between two points may be detected. This is possible due to the fact that the multiple-window antenna 6 comprises several radiating elements having a mutual distance which is known. In this embodiment, merely a distance in two-dimensional space between the two transmitter/receiver devices 2 and 2' is detected, for which reason the multiple-window antenna 6 only includes two radiating elements. It is, however, also possible to expand this application through the provision of further transmitter/receiver devices 2 and of a suitable multiple-window antenna 6 having a suitable number of radiating elements, such that distances and thus positional changes in three-dimensional space between any number of transmitter/receiver devices 2 may be detected.

In order to detect a positional change of the transmitter/receiver device 2', at one time the mutual distance of the first and second transmitter/receiver devices 2 and 2' is determined.

FIG. 4A shows an arrangement of the first transmitter/receiver device 2, second transmitter/receiver device 2', and multiple-window antenna 6 including two radiating elements having a distance which is known.

Figure 4B:
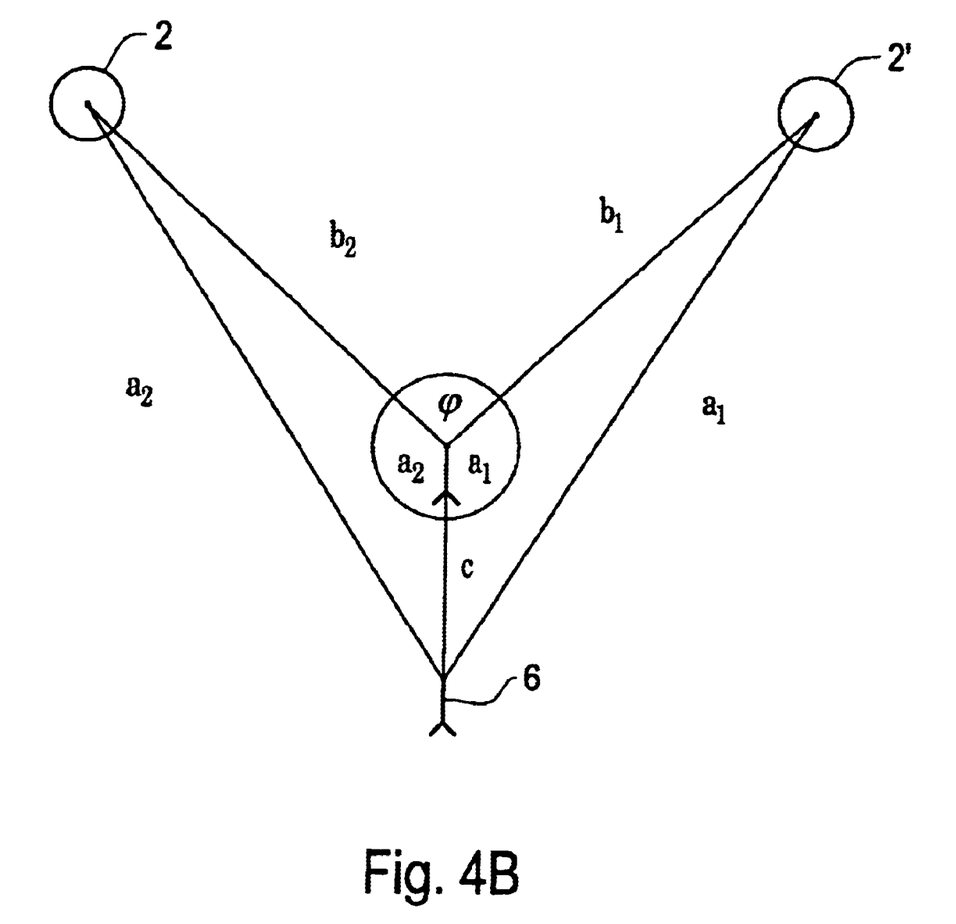

At first, in accordance with the representation of FIG. 4B, the distances of the two transmitter/receiver devices 2 and 2' from the multiple antenna 6 are determined in that the multiple antenna 6 transmits a signal to the first and second transmitting and receiving devices 2 and 2', having the result that the transmitter/receiver devices transmit a signal back to the multiple antenna, so that there is the possibility of determining the distances of the two transmitter/receiver devices 2 and 2' from the radiating elements of the multiple antenna by way of the signal propagation time.

Figure 4C:
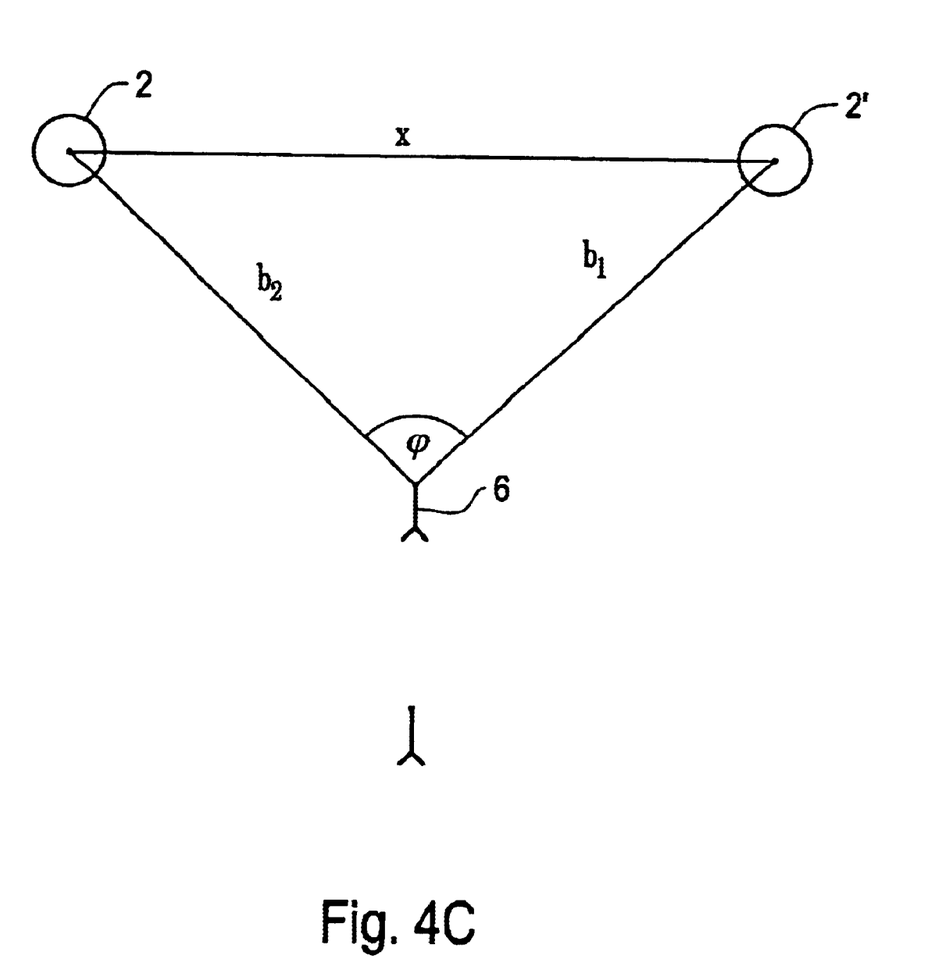

This furthermore opens up the possibility of determining the distance between the first and second transmitter/receiver devices by means of two determined distances and angles which may be calculated by the cosine emission law by renewed application of the cosine emission law, as is shown in FIG. 4C.

Figure 4D:
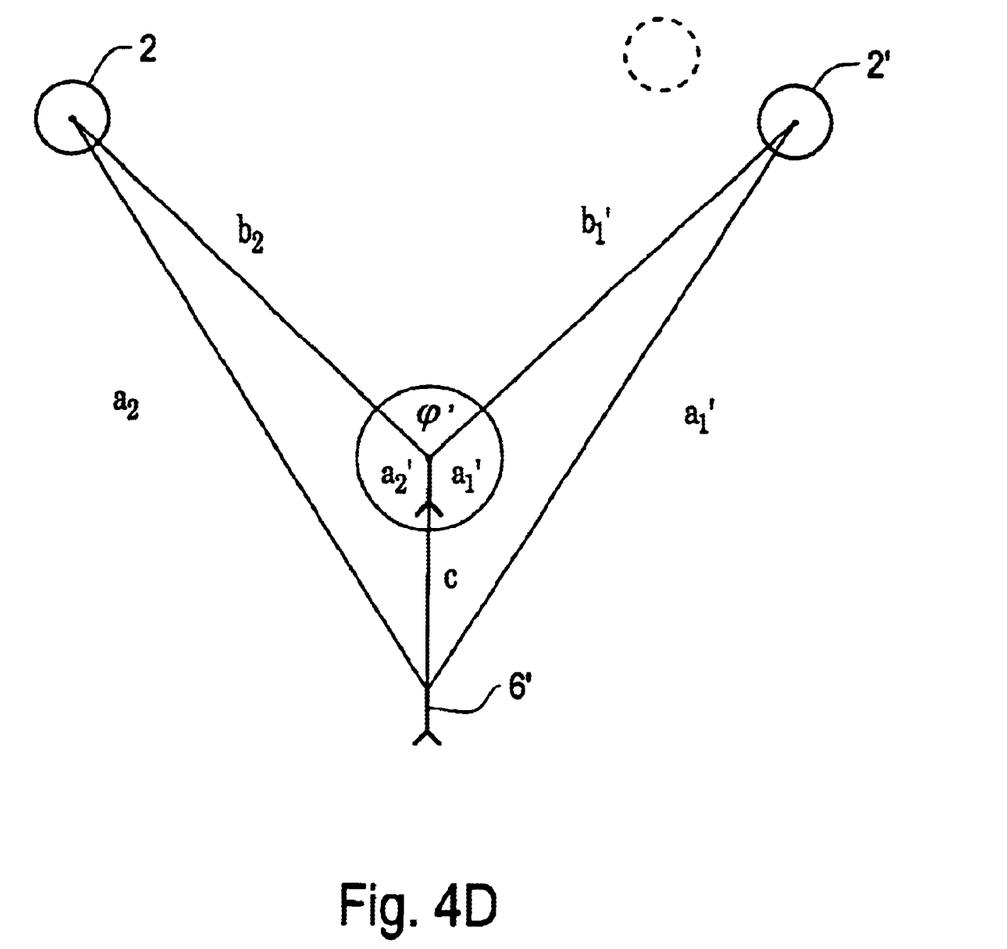
Figure 4E:
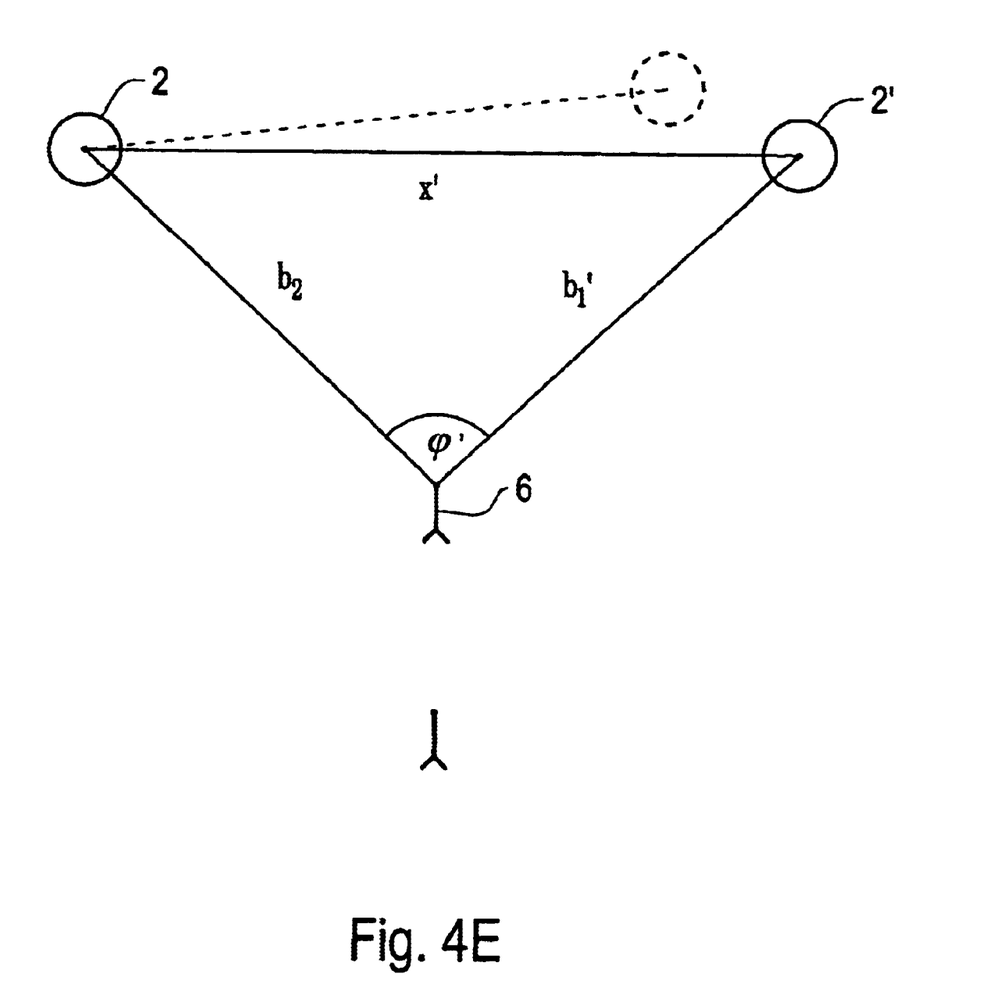

If, now, in accordance with the representation in FIG. 4D the position of the second transmitter/receiver device changes, the above mentioned process may be repeated in accordance with the representation of FIGS. 4D and FIG. 4E to determine a positional change by means of the difference between the determined distances.

With the aid of this application it is thus possible to detect a positional change in a simple manner. Data indicating a respectively present position of the second transmitter/receiver device 2' relative to a point of reference, i.e. the first transmitter/receiver device 2, are stored contactless with the aid of the sensor device 3 in one or both of the transmitter/receiver devices 2 and 2' or generally in any number of respectively present transmitter/receiver devices 2.

With regard to further features and advantages of the present invention, reference is expressly made to the disclosure of the drawings.

While preferred embodiments of the present invention and modifications thereof have been shown and described, it will be understood that there is no intent to limit the present invention by such disclosure but rather it is intended to cover all modifications falling within the spirit and scope of the present invention as defined in the appended claims.

What is claimed is:

1. Apparatus for monitoring implants contained inside a living body, comprising:

at least one transmitter/receiver device which is introduceable into the living body and in which data relating to the implant may be stored, wherein the data relating to the implant may be written into said at least one transmitter/receiver device and read from it contactlessly with the aid of an external write-read device located externally of the living body; and at least one sensor device for monitoring at least one temporally variable state parameter of the implant and for transmitting data corresponding to a currently prevailing state to said at least one transmitter/receiver device in accordance with a detected value of the least one temporally variable state parameter, wherein the data corresponding to the currently prevailing stare is written into said at least one transmitter/receiver device in response to transmission from said at least one sensor device.

2. Apparatus according to claim 1, wherein the data corresponding to the currently prevailing state, which is stored in said at least one transmitter/receiver device, is readable with the aid of said external write-read device.

3. Apparatus according to claim 1, wherein said at least one transmitter/receiver device is a transponder.

4. Apparatus according to claim 1, wherein said at least one sensor device detects a value of a physical function, a value of a physiological function, or a combination of these as the temporally variable state parameter.

5. Apparatus according to claim 1, further comprising fixing means whereby it may be fixed inside the living body.

6. Apparatus according to claim 1, wherein the data corresponding to the currently prevailing state is written directly into said at least one transmitter/receiver device in response to transmission from said at least one sensor device.

7. Apparatus according to claim 1, wherein the data corresponding to the currently prevailing state is written into said at least one transmitter/receiver device by means of said external device in response to transmission from said at least one sensor device.

8. System including an apparatus for monitoring implants contained inside a living body, and an external write-read device, wherein said apparatus for monitoring implants contained inside a living body comprises:

at least one transmitter/receiver device which is introduceable into the living body and in which data relating to the implant may be stored, wherein the data relating to the implant may be written into said at least one transmitter/receiver device and read from it contactlessly with the aid of said external write-read device located externally of the living body; and at least one sensor device for monitoring at least one temporally variable state parameter of the implant and for transmitting data corresponding to a currently prevailing state to said at least one transmitter/receiver device in accordance with a detected value of the at least one temporally variable state parameter, wherein the data corresponding to the currently prevailing state is written into said at least one transmitter/receiver device in response to transmission from said at least one sensor device.

9. System according to claim 8, wherein the data corresponding to the currently prevailing state, which is stored in said at least one transmitter/receiver device, is readable with the aid of said external write-read device.

10. System according to claim 8, wherein said at least one transmitter/receiver device is a transponder.

11. System according to any claim 8, wherein said at least one sensor device detects a value of a physical function, a value of a physiological function, or a combination of these as the temporally variable state parameter.

12. System according to claim 8, wherein said apparatus for monitoring implants contained inside a living body further comprises fixing means whereby it may be fixed inside the living body.

13. System according to claim 8, wherein the data corresponding to the currently prevailing state is written directly into said at least one transmitter/receiver device in response to transmission from said at least one sensor device.

14. Apparatus according to claim 8, wherein the data corresponding to the currently prevailing state is written into said at least one transmitter/receiver device by means of said external device in response to transmission from said at least one sensor device.

* * * * *